(12) United States Patent
Colson et al.

(10) Patent No.: US 9,237,948 B2
(45) Date of Patent: Jan. 19, 2016

(54) DELIVERY SYSTEM WITH PROJECTIONS

(71) Applicant: Medtronic, Inc., Minneapolis, MN (US)

(72) Inventors: Michael A. Colson, Mounds View, MN (US); Declan P. Costello, Ballybrit (IE); Barry O'Connell, Ballybrit (IE)

(73) Assignee: Medtronic, Inc., Minneapolis, MN (US)

( * ) Notice: Subject to any disclaimer, the term of this patent is extended or adjusted under 35 U.S.C. 154(b) by 147 days.

(21) Appl. No.: 13/939,612

(22) Filed: Jul. 11, 2013

(65) Prior Publication Data

US 2015/0018939 A1  Jan. 15, 2015

(51) Int. Cl.
*A61F 2/24* (2006.01)

(52) U.S. Cl.
CPC .............. *A61F 2/243* (2013.01); *A61F 2/2436* (2013.01); *A61F 2220/0008* (2013.01); *A61F 2230/005* (2013.01); *A61F 2230/0013* (2013.01)

(58) Field of Classification Search
CPC ............... A61F 2/2436; A61F 2/2418; A61F 2002/9505; A61F 2/2427; A61F 2/243
USPC .............. 623/1.11–1.13, 1.23, 2.11; 606/108
See application file for complete search history.

(56) References Cited

U.S. PATENT DOCUMENTS

| | | | |
|---|---|---|---|
| 6,629,534 B1 | 10/2003 | St. Goar et al. | |
| 7,785,341 B2 | 8/2010 | Forster et al. | |
| 2004/0003819 A1 | 1/2004 | St. Goar et al. | |
| 2007/0088431 A1 | 4/2007 | Bourang et al. | |
| 2008/0009746 A1 | 1/2008 | Forster et al. | |
| 2008/0033543 A1 | 2/2008 | Gurskis et al. | |
| 2009/0228093 A1 | 9/2009 | Taylor et al. | |
| 2010/0121436 A1 | 5/2010 | Tuval et al. | |
| 2010/0191326 A1* | 7/2010 | Alkhatib ...................... 623/2.11 |
| 2011/0022157 A1 | 1/2011 | Essinger et al. | |
| 2011/0251676 A1* | 10/2011 | Sweeney et al. ............. 623/1.23 |
| 2011/0264200 A1 | 10/2011 | Tran et al. | |
| 2012/0022633 A1* | 1/2012 | Olson et al. .................. 623/1.11 |
| 2013/0073032 A1 | 3/2013 | Wang | |

FOREIGN PATENT DOCUMENTS

WO  WO2012083070  6/2012

OTHER PUBLICATIONS

PCT/US2014/45294, PCT International Search Report and Written Opinion, mailed Oct. 9, 2014.

* cited by examiner

Primary Examiner — Katherine M Shi

(57) ABSTRACT

Delivery systems for delivering medical devices and prosthetic heart valves in a patient's body are disclosed. The delivery system may include a catheter-based delivery system. The delivery system may include a tip, a capsule, an inner sheath, and a projection. The delivery system may include an outer sheath and a handle. The delivery system may be configured to be actuated via an actuator disposed on the handle. The projection may include an arm portion and a feeler portion. The feeler portion may include an indentation. The delivery system may be configured to correctly position a medical device or prosthetic heart valve.

18 Claims, 7 Drawing Sheets

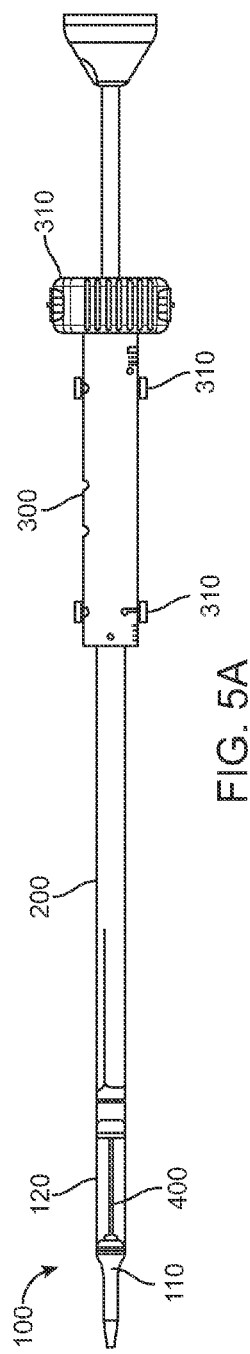
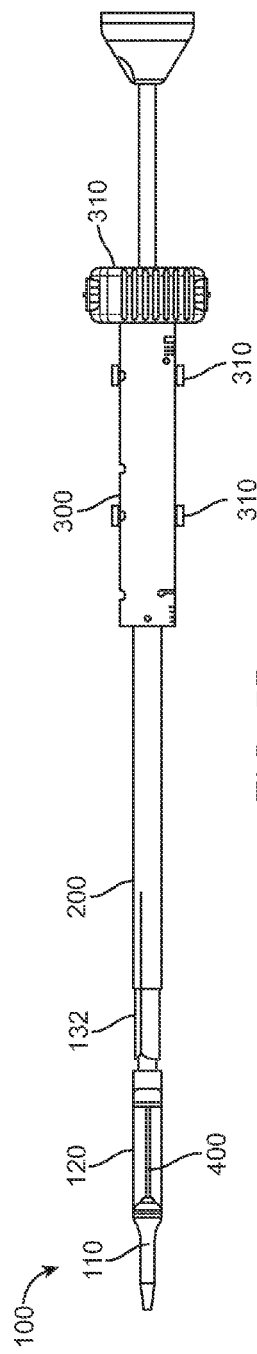
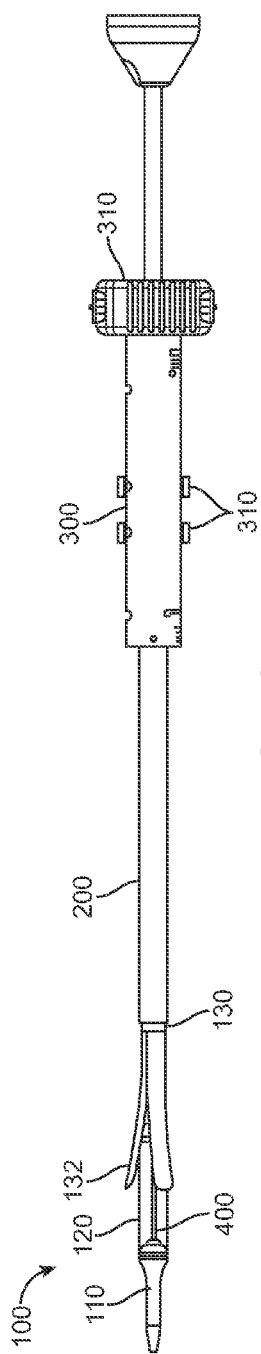
FIG. 5A
FIG. 5B
FIG. 5C

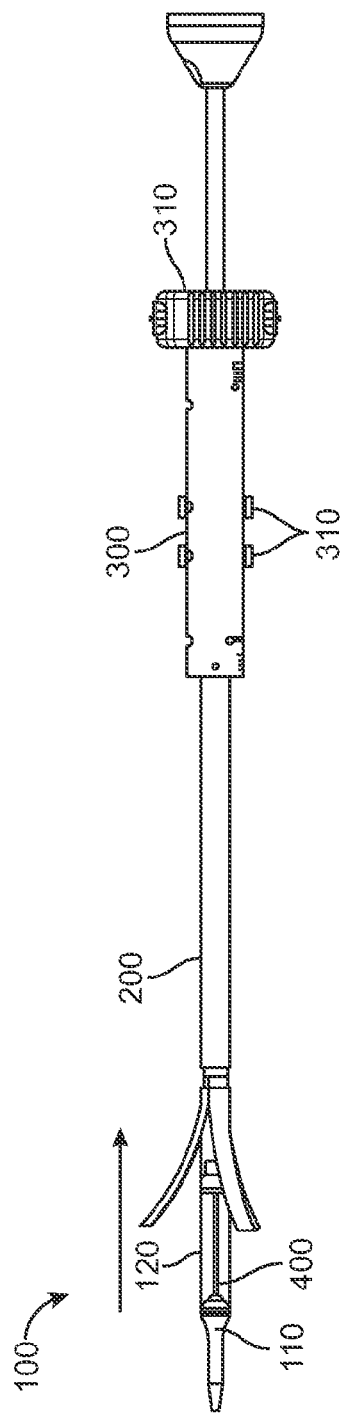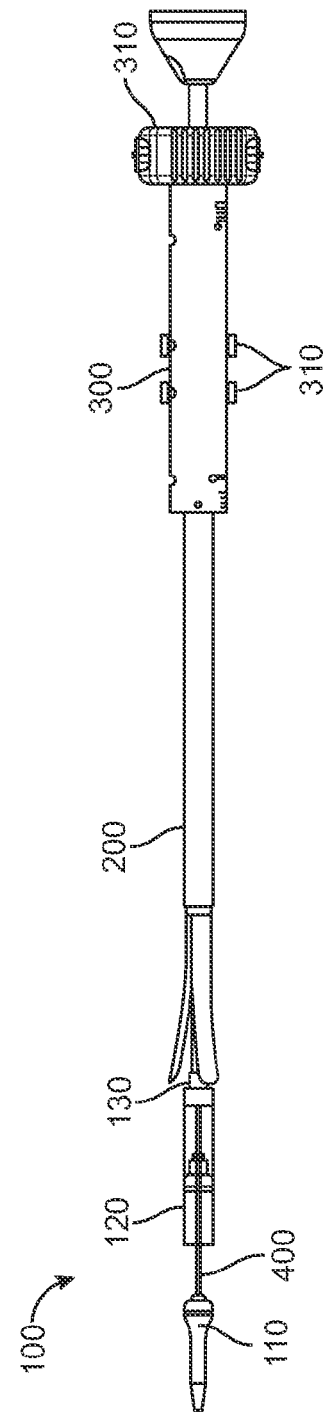
FIG. 5D
FIG. 5E

DELIVERY SYSTEM WITH PROJECTIONS

BACKGROUND

In many medical procedures, a delivery system is used to place a medical device, such as a prosthetic heart valve, in a patient. Often a prosthetic heart valve is disposed on a delivery system in order to be placed in a patient. One type of delivery system is a catheter, which can deliver the prosthetic heart valve via a transfemoral procedure. As part of this procedure the prosthetic heart valve must be positioned in the patient. Visualization techniques such as fluoroscopy may be used to locate the native heart valve components and align the prosthetic heart valve in the patient, but can require substantial contrast medium exposure to the patient, increased risk, and can be difficult.

Further, some current prosthetic heart valves employ projections or arms to aid in retention of the prosthetic heart valve. However, these control, engagement, or support arms increase the profile of the prosthetic heart valve making the overall profile of the prosthetic heart valve and delivery system larger. Other current prosthetic heart valves are not configured to include control arms and physicians are unable to utilize the benefits of these control arms in procedures involving such prosthetic heart valves.

BRIEF SUMMARY

In some embodiments a delivery system comprises a projection or a support arm structure. Employing a projection or support arm on the delivery system provides advantages. Having a projection on the delivery system as opposed to on a medical device or a prosthetic heart valve will lower the profile of the prosthetic heart valve and delivery system. This lower profile allows for better control and manipulation by a physician. In addition, employing projections on a delivery system allows for advantages when used with medical devices or prosthetic heart valves that do not or cannot employ similar projections. For example, some heart valves do not or cannot use control arms for various reasons. Having projections on the delivery system permits the delivery system to be used with these prosthetic heart valves while also providing advantages associated with such projections. For example, the projections on the delivery system may provide tactile feedback in positioning the heart valve. As another example, the projections may be configured to aid in aligning a prosthetic heart valve with a native heart valve.

The support arm structure or projections can locate the prosthetic heart valve relative to a native heart valve. The support arm structure provides a way to give tactile feedback of the location of the prosthetic heart valve as well as the native valve and surrounding area to a physician or surgeon. Thus, the support arm structure provides an advantage to the physician in implanting prosthetic heart valves and other devices. Another potential advantage of this type of support arm structure is to limit the amount of fluoroscopy used or contrast medium required to place a prosthetic heart valve within the patient.

In some embodiments the support arm structure or projection is part of a delivery system. In some embodiments this delivery system is catheter-based. In some embodiments any type of prosthetic heart valve could be placed in or on a delivery system that includes support arms or projections. These prosthetic valve types would include aortic, mitral, or other valve types, including balloon expandable, mechanically expandable, self-expandable, or surgical suture-less valves. Any prosthetic valve type could be used in conjunction with the delivery system that comprises a support, engagement, or control arm or projection.

The support arms or projections can provide mechanical or tactile feedback. In some embodiments this projection or support arm structure can provide enough feedback to limit visualization techniques required to correctly position the prosthetic heart valve inside the patient's heart. In some embodiments the projection or support arm structure may provide enough feedback and information regarding the position of the prosthetic heart valves, such that no visualization technique may be required. In some embodiments using the projection without requiring visualization techniques will be advantageous. For example, these visualization techniques may be unavailable, be potentially dangerous to the patient, or foregoing such visualization may reduce associated risks. In some embodiments these projections or support arm structures will minimize the amount of contrast medium used in examining the patient and will reduce the subsequent associated renal problems associated with contrast medium exposure.

In some embodiments the projection or support arm structure will provide feedback regarding orientation. In some embodiments the projection will aid in rotational positioning of the prosthetic heart valve. In some embodiments the projection will aid in axial positioning of the prosthetic heart valve.

In some embodiments, the delivery device may include a catheter and the catheter may include a tip, a capsule adjacent the tip, and an inner sheath adjacent the capsule.

In some embodiments the inner sheath is disposed along a longitudinal axis, an outer sheath is disposed along the longitudinal axis and connected to a handle, and the handle further comprising an actuator.

In some embodiments the inner sheath comprises projections distal the handle. In some embodiments the actuator is configured to actuate the outer sheath. In some embodiments the capsule is configured to receive a medical device. In some embodiments the outer sheath is configured to move along the longitudinal axis to expose the projections. In some embodiments the projections are configured to open outward from the longitudinal axis.

In some embodiments the projections are asymmetric.

In some embodiments each projection is uniquely shaped.

In some embodiments the projections are configured to evenly space from each other when they are rotated outward.

In some embodiments each projection comprises an arm portion and a feeler portion, the feeler portion having a proximal and distal end.

In some embodiments the feeler portion has a substantially straight distal end.

In some embodiments the feeler portion comprises protrusions extending away from the arm portion.

In some embodiments the feeler portion comprises a curved end on the distal most end, and wherein the feeler portion further comprises a notch.

In some embodiments the feeler portion is symmetric.

In some embodiments the feeler portion is asymmetric.

In some embodiments there exists a method of delivering a prosthetic heart valve, the method including advancing a delivery system into a patient's heart having native commissures, the delivery system including a catheter.

In some embodiments the catheter comprises a tip, a capsule adjacent the tip, an inner sheath adjacent the capsule, and the inner sheath being disposed along a longitudinal axis, an outer sheath configured to move along the longitudinal axis and connected to a handle.

In some embodiments the handle further comprises an actuator, the inner sheath has a proximal end and a distal end, and the inner sheath being disposed along a longitudinal axis.

In some embodiments the inner sheath comprises projections proximal the capsule. In some embodiments the projections are configured to rotate outward from the longitudinal axis. In some embodiments the actuator is configured to actuate the outer sheath. In some embodiments the capsule contains a prosthetic heart valve configured to collapse to a collapsible state and expand to an expanded state.

In some embodiments the method includes retracting the outer sheath. In some embodiments the method includes advancing the projections proximate the capsule. In some embodiments the method includes causing the projections to rotate outward from the longitudinal axis. In some embodiments the method includes expanding the prosthetic heart valve to an expanded state. In some embodiments the method includes anchoring the prosthetic heart valve in the patient's heart.

In some embodiments the projections further comprise an arm portion and a feeler portion, the method further comprising using the projections to position the prosthetic heart valve.

In some embodiments the method further comprises using the projections to position the prosthetic heart valve by aligning a portion of the feeler portion of one projection with a portion of the patient's heart.

In some embodiments the feeler portion of one projection further comprises a notch, the method further comprising using the projections to position the prosthetic heart valve by aligning the notch of the projection with a portion of the patient's heart.

In some embodiments the feeler portion of one projection further comprises a channel, the method further comprising using the projections to position the prosthetic heart valve by aligning the channel of one projection with a portion of the patient's heart.

In some embodiments the method further comprising generating a fluoroscopic image positioning the prosthetic heart valve based on the position of one projection relative to a portion of the patient's heart.

In some embodiments an assembly for delivering a prosthetic heart valve is disclosed. In some embodiments the assembly comprises a tip, a capsule adjacent the tip, an inner sheath adjacent the capsule, the inner sheath being disposed along a longitudinal axis, an outer sheath being disposed along the longitudinal axis, a handle coupled to the outer sheath, and the handle further comprising an actuator.

In some embodiments wherein the inner sheath comprises a projection distal the handle. In some embodiments the actuator is configured to actuate the outer sheath. In some embodiments the capsule is configured to receive a prosthetic heart valve. In some embodiments the outer sheath is configured to expose the projection. In some embodiments the projection is configured to extend away from the longitudinal axis.

In some embodiments the projection further comprises an indentation on the distal end.

In some embodiments the projection is configured to be positioned relative to a native commissure by using fluoroscopic imaging.

In some embodiments the projection further comprises an asymmetric shape.

The embodiments and related concepts will be more fully understood from the following detailed description of the embodiments thereof.

BRIEF DESCRIPTION OF THE FIGURES

FIGS. 5A-5E illustrate a delivery system in accordance with some embodiments.

DETAILED DESCRIPTION OF EMBODIMENTS

Figure 1:
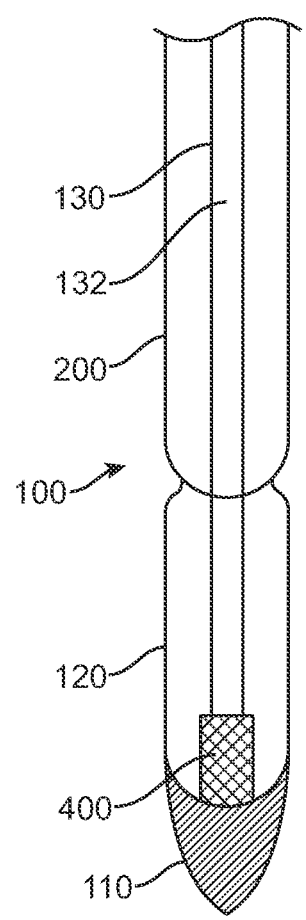
FIGS. 1-3 illustrate a delivery system in accordance with some embodiments.

While the disclosure refers to illustrative embodiments for particular embodiments, it should be understood that the disclosure is not limited thereto. Modifications can be made to the embodiments described herein without departing from the spirit and scope of the present disclosure. Those skilled in the art with access to this disclosure will recognize additional modifications, embodiments, and embodiments within the scope of this disclosure and additional fields, in which the disclosed examples could be applied. Therefore, the following detailed description is not meant to be limiting. Further, it is understood that the apparatus and methods described below can be implemented in many different embodiments of hardware. Any actual hardware described is not meant to be limiting. The operation and behavior of the apparatus and methods presented are described with the understanding that modifications and variations of the embodiments are possible.

References to "one embodiment," "an embodiment," "some embodiments," "in certain embodiments," etc. . . . , indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

In some embodiments the delivery system will include a catheter-based delivery system. In some embodiments catheter 100 will include multiple elements. In some embodiments catheter 100 may include a distal tip 110, a capsule 120, and inner sheath 130. In some embodiments inner sheath 130 may include one projection 132. In some embodiments inner sheath 130 may include multiple projections 132. In some embodiments projections 132 may include an arm portion 134. In some embodiments projections 132 may include a feeler portion 136. In some embodiments projections 132 may include an indentation 138 as part of feeler portion 136. In some embodiments projections 132 are separate from inner sheath 130.

In some embodiments catheter 100 may include projections 132 that are connected to inner sheath 130. In some embodiments catheter 100 may include projections 132 that are integral with inner sheath 130. In some embodiments inner sheath 130 may include two projections 132. In some embodiments inner sheath 130 may include more than two projections 132.

In some embodiments the delivery system may also include an outer sheath 200. In some embodiments the delivery system may include a proximal handle 300. In some embodiments handle 300 may also include an actuator 310.

In some embodiments the delivery system is configured to receive a medical device 400. In some embodiments the delivery system includes catheter 100 configured such that medical device 400 can be contained in capsule 120. In some embodiments the delivery system includes catheter 100 configured such that medical device 400 can be disposed on capsule 120. In some embodiments medical device 400 may comprise a prosthetic heart valve and/or a prosthetic heart valve repair device.

In some embodiments the delivery system includes catheter 100 configured such that prosthetic heart valve 500 can be contained in capsule 120. In some embodiments the delivery system includes catheter 100 configured such that prosthetic heart valve 500 can be disposed on capsule 120.

In some embodiments prosthetic heart valve 500 may include two or three or more commissural posts 510. In some embodiments prosthetic heart valve 500 may include one, two, or more commissural posts 510.

In some embodiments catheter 100 comprises a tip 110, a capsule 120, and inner sheath 130. In some embodiments the tip is disposed at the distal end of catheter 100. In some embodiments the capsule 120 is adjacent the tip 110. In some embodiments the inner sheath 130 is adjacent the capsule 120. In some embodiments capsule 120 may comprise a split capsule having two or more portions.

In some embodiments the inner sheath 130 is disposed along a longitudinal axis. In some embodiments the outer sheath 200 is disposed along a longitudinal axis. In some embodiments the outer sheath 200 is disposed along the same longitudinal axis as the inner sheath 130.

In some embodiments the outer sheath 200 is connected to a handle 300. In some embodiments the inner sheath 130 comprises projections 132 distal the handle 300. In some embodiments actuator 310 is configured to actuate outer sheath 200. In some embodiments outer sheath 200 is configured to move along a longitudinal axis to expose the projections 132. In some embodiments the projections 132 are configured to open outward from the longitudinal axis. In some embodiments the actuator 310 is configured to actuate any part of the delivery system.

In some embodiments the delivery system can be used to deliver a prosthetic heart valve 500 into a patient's heart 610. In some embodiments a patient 600 has a heart 610 that includes native commissures 612, a native valve 614, and native commissural sinuses 616.

In some embodiments a method of delivering a prosthetic heart valve 500 includes advancing catheter 100 into a patient's heart 600 that has a native commissure 612. In some embodiments the capsule 120 is configured to contain a prosthetic heart valve 500.

In some embodiments the prosthetic heart valve 500 is configured to collapse to a collapsed state. In some embodiments the prosthetic heart valve 500 is configured to expand to an expanded state. In some embodiments the method of delivering a prosthetic heart valve 500 further includes retracting the outer sheath 200 after the catheter 100 has been advanced into a patient's heart 610. In some embodiments the method further includes advancing the projection 132 or projections 132 proximate the capsule 120. In some embodiments the method further includes causing a projection 132 to rotate outward from the longitudinal axis and away from the catheter 100. In some embodiments the method further includes expanding the prosthetic heart valve 500 to an expanded state. In some embodiments the method further includes anchoring the prosthetic heart valve 500 in a patient's heart 610.

FIG. 1 illustrates a delivery device in accordance with some embodiments. FIG. 1 illustrates a catheter 100. In some embodiments catheter 100 includes tip 110, capsule 120, and inner sheath 130. In some embodiments, tip 110 may comprise different geometries including a narrowed end portion, as shown in FIG. 1, a blunt tip, or a purely cylindrical tip. Tip 110 can vary in length.

In some embodiments capsule 120 may vary in length. In some embodiments capsule 120 may be shorter or longer than tip 110. In some embodiments capsule 120 may be wider or narrower than tip 110. In some embodiments capsule 120 may be wider or narrower in diameter, circumference, or perimeter than any or all portions of tip 110. In some embodiments tip 110 may comprise capsule 120. In some embodiments tip 110 may comprise a distal portion of capsule 120.

In some embodiments, the capsule portion may be configured to contain a medical device 400 as illustrated in FIG. 1. In some embodiments capsule 120 may be configured to contain a prosthetic heart valve 500. In some embodiments a medical device 400 can be disposed on capsule 120. In some embodiments a medical device 400 can be disposed in capsule 120. In some embodiments a medical device 400 can be disposed on another portion of catheter 100. In some embodiments prosthetic heart valve 500 may be configured to be disposed on capsule 120. In some embodiments prosthetic heart valve 500 may be configured to be disposed in capsule 120. In some embodiments prosthetic heart valve 500 may be configured to be disposed on another portion of catheter 100.

In some embodiments capsule 120 can also have the same characteristics related to inner sheath 130. In some embodiments capsule 120 may be shorter or longer than inner sheath 130. In some embodiments capsule 120 may be wider or narrower inner sheath 130. In some embodiments capsule 120 may be wider or narrower in diameter, circumference, or perimeter than any or all portions of inner sheath 130.

In some embodiments, the delivery system may comprise an outer sheath 200 as illustrated in FIG. 1. In some embodiments outer sheath 200 may be configured to extend and cover tip 100. In some embodiments outer sheath 200 may be configured to extend and cover capsule 120. In some embodiments outer sheath 200 may be configured to extend and cover inner sheath 130. In some embodiments outer sheath 200 may be configured to extend and surround tip 100. In some embodiments outer sheath 200 may be configured to extend and surround capsule 120. In some embodiments outer sheath 200 may be configured to extend and surround inner sheath 130. In some embodiments outer sheath 200 may comprise capsule 120. In some embodiments outer sheath 200 may comprise a proximal portion of capsule 120.

In some embodiments outer sheath 200 may be configured to cover or surround a projection 132 disposed on inner sheath 130. In some embodiments outer sheath 200 may be configured to cover or surround a projection 132 that is an integral part of inner sheath 130. In some embodiments outer sheath 200 may be configured to cover or surround a projection 132 that is positioned between inner sheath 130 and outer sheath 200.

Figure 2:
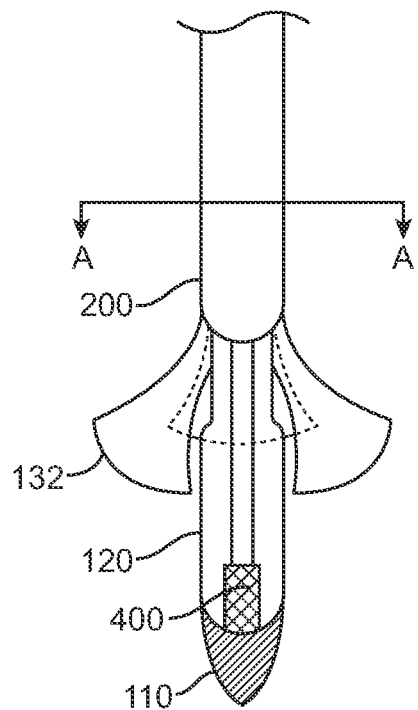
Figure 2:
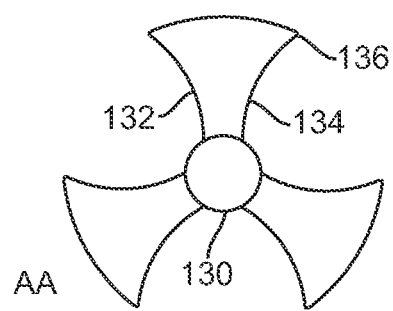

FIG. 2 illustrates some embodiments of a delivery system. In some embodiments the delivery system includes catheter 100 and projections 132. In some embodiments catheter 100 includes outer sheath 200. In some embodiments catheter 100 includes capsule 120. In some embodiments catheter 100 includes tip 110 disposed at an end of the catheter 100. In some embodiments outer sheath 200 is configured to move or retract proximally thereby exposing a projection 132. In some embodiments outer sheath 200 is configured to move or retract proximally thereby exposing multiple projections 132. In some embodiments outer sheath 200 is configured to be actuated to expose a projection 132.

In some embodiments when outer sheath 200 is retracted proximally the projection 132 or projections 132 or portions thereof are configured to automatically rotate, flex, bend, and/or spring outward from inner sheath 130 and/or capsule 120. In some embodiments a projection 132 is configured to move away from capsule 120 when outer sheath 200 is removed from at least a portion of catheter 100. In some embodiments a projection 132 is configured to move away from capsule 120 when outer sheath 200 is removed from at least a portion of inner sheath 130.

In some embodiments when outer sheath 200 is retracted proximally the capsule 120 remains in the same position. In some embodiments when capsule 120 remains in the same position medical device 400 which may be contained in capsule 120 remains in a collapsed state.

In some embodiments when outer sheath 200 is retracted a proximal distance at least one projection 132 is exposed and rotates, flexes, bends, and/or springs outwardly away from catheter 100. In some embodiments when outer sheath 200 is retracted proximally an additional distance at least one other projection 132 will rotate, flex, bend, and/or spring outward away from catheter 100. In some embodiments when outer sheath 200 is retracted a proximal distance, at least one projection 132 is exposed and rotates, flexes, bends, and/or springs outwardly away from capsule 120. In some embodiments when outer sheath 200 is retracted an additional proximal distance at least one other projection 132 will rotate, flex, bend, and/or spring outward away from capsule 120.

In some embodiments as illustrated in section view A-A of FIG. 2, the three projections 132 are disposed radially. In some embodiments the projections 132 are disposed with equal distance between the projections 132. In some embodiments the projections 132 are disposed with non-equal distance between the projections 132.

In some embodiments each projection 132 extends from a portion of inner sheath 130.

In some embodiments projections 132 are made of varying shapes. In some embodiments projections 132 include an arm portion 134. In some embodiments arm portion 134 includes a portion of projection 132 proximate the inner sheath 130. In some embodiments projection 132 includes a feeler portion 136. In some embodiments feeler portion 136 is disposed adjacent arm portion 134. In some embodiments feeler portion 136 is disposed adjacent arm portion 134, which is disposed adjacent inner sheath 130. In some embodiments feeler portion 136 is distal inner sheath 130.

In some embodiments projections 132 are configured to be rotatable by manipulating catheter 100. In some embodiments projections 132 are configured to be rotatable by manipulating inner sheath 130. By rotating a projection 132 a person can position the medical device 400 or a prosthetic heart valve 500 within a patient 600.

Section view AA of FIG. 2 illustrates the potential ability of multiple projections 132 to rotate either clockwise or counterclockwise, as needed, to position medical device 400 or prosthetic heart valve 500.

Figure 3:
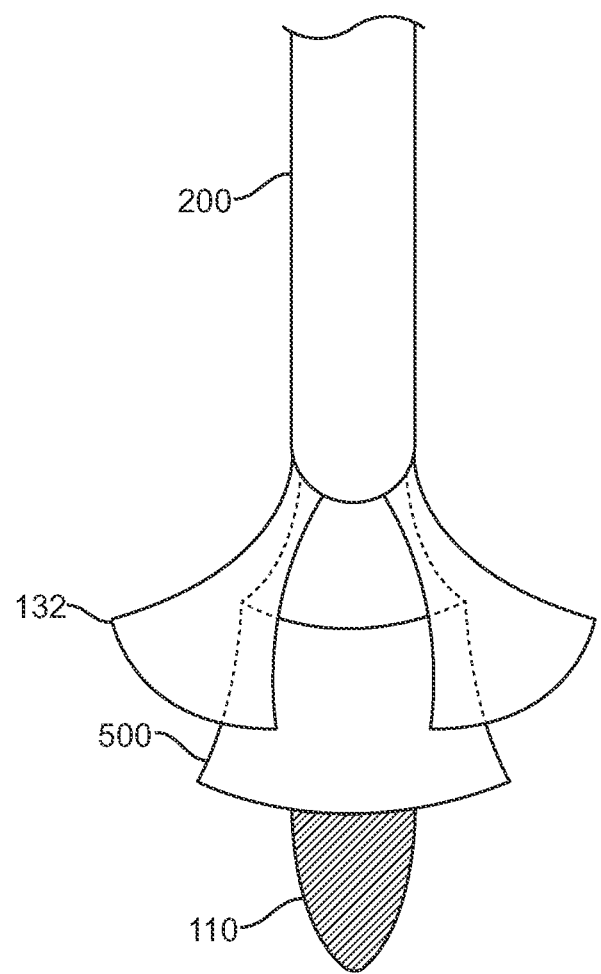

In some embodiments, as illustrated in FIG. 3, the projections 132 can aid in positioning a medical device 400 or a prosthetic heart valve 500. In some embodiments capsule 120 is moved such that prosthetic heart valve 500 can be deployed. FIG. 3 illustrates a prosthetic heart valve 500 being disposed on catheter 100. Catheter 100 may include tip 110 and capsule 120. Capsule 120 may be configured such that it can be retracted proximally up into outer sheath 200. Capsule 120 may be configured such that it can be retracted proximally away from tip 110. In some embodiments the retraction of capsule 120 up into outer sheath 200 will allow prosthetic heart valve 500 to expand to an expanded state. In some embodiments the retraction of capsule 120 along with some actuation will allow prosthetic heart valve 500 to expand to an expanded state. In some embodiments prosthetic heart valves 500 may be disposed on capsule 120. In some embodiments prosthetic heart valves 500 may be disposed in capsule 120.

The projections 132 may be comprised of any suitable material that can be introduced into a subject. This would include, but is not limited to, metals, plastics, polymers, a biocompatible material, biological material, and any other suitable material known to a person of ordinary skill in the art.

As illustrated in FIGS. 4A-4D a projection 132 or projections 132 may have various shapes and profiles. Projection 132 may comprise one material or multiple materials. Projection 132 may comprise one piece or multiple pieces. In some embodiments the multiple pieces comprising projection 132 may be joined, attached, or coupled to each other. Projection 132 may be solid or may be an outline formed into a desired shape. Projection 132 may comprise an aperture or apertures in the solid. The outline of projection 132 may also define one or more apertures. In some embodiments the solid or outline shape may be formed from wire, such as nitinol, other shape memory metals, or an alloy. In some embodiments the solid or outline shape may be formed from a plastic or a polymer. In some embodiments the solid or outline shape may be formed from another biocompatible material. Projection 132 may comprise a leaf, petal, elongate, tab, asymmetric, or other suitable shape.

Figure 4A:
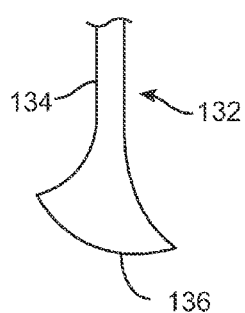
FIGS. 4A-4D illustrate a portion of a delivery system in accordance with some embodiments.

FIG. 4A illustrates some embodiments. In some embodiments a projection 132 may comprise an arm portion 134. In some embodiments a projection 132 may comprise a feeler portion 136. In some embodiments a projection 132 may comprise an arm portion 134 and a feeler portion 136. In some embodiments the arm portion of 134 may have different lengths for each side of the arm portion. In some embodiments the arm portion of 134 may have two different lengths for each edge of the arm portion 134. As can be seen in FIG. 4A the length of the left side or left edge of the projection 132 is shorter than the right side or edge of the projection 132.

In some embodiments a projection 132 may be asymmetric. In some embodiments a projection 132 may be symmetric. In some embodiments the side of a projection 132 may comprise an arc portion. In some embodiments the projection 132 may comprise a substantially straight portion and an arc portion on one side or edge. In some embodiments a projection 132 may have a side or edge that is substantially straight portion, an arc portion, and another substantially straight portion of the projection 132. In some embodiments the arm portion 134 can have different shapes for each side of one projection 132.

In some embodiments the projection 132 can have different shapes for each side or edge. In some embodiments the projection 132 may have a circular profile.

In some embodiments comprising multiple projections 132, each projection 132 may include an arm portion 134 and a feeler portion 136. In some embodiments the feeler portion 136 may comprise an arc section, a flat section, or a substantially straight section In some embodiments the feeler portion 136 of projection 132 may include a section shaped similar to the shape of a sinus 116 in a heart. In some embodiments the feeler portion 136 may be asymmetric. In some embodiments the feeler portion 136 may be symmetric. In some embodiments the arm portion 134 may be asymmetric. In some embodiments the arm portion 134 may be symmetric.

Figure 4B:
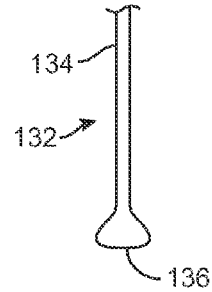
Figure 4C:
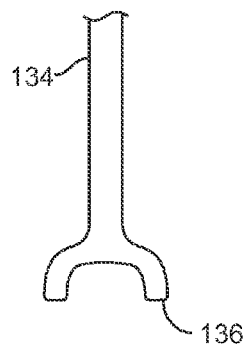

In some embodiments, as shown in FIG. 4B, a projection 132 may include an arm portion 134 comprised of substantially straight sections. In some embodiments the arm portion 134 may include edges that are substantially parallel to one another for at least some length of the arm portion 134. In some embodiments the edges of arm portion 134 may not be substantially parallel.

In some embodiments feeler portion 136 can have a varying width. In some embodiments arm portion 134 can have a varying width. In some embodiments feeler portion 136 may have a width different from arm portion 134. In some embodiments feeler portion 136 may be narrower than arm portion 134. In some embodiments feeler portion 136 may be wider than arm portion 134. In some embodiments the width of the feeler portion 136 at one point may be greater than the width of the arm portion 134 at one point. In some embodiments the width of the feeler portion 136 at every point may be greater than the width of the arm portion 134 at every point. In some embodiments the width of feeler portion 136 may be less than the width of arm portion 134. In some embodiments the width of feeler portion 136 may be more than double the width of arm portion 134. In some embodiments the width of the feeler portion 136 at the widest point may be more than double the width of an arm portion 134 at its narrowest point.

In some embodiments the distal end of feeler portion 136 may be substantially straight. In some embodiments the distal end of feeler portion 136 may be an arc. In some embodiments the distal end of feeler portion 136 may be not straight.

In some embodiments, the arm portion 134 can be of varying width along at least a portion of the length of arm portion 134. In some embodiments the feeler portion 136 may include protrusions or extensions. In some embodiments the feeler portion 136 may include one or more protrusions. In some embodiments the feeler portion 136 may include an indentation 138. In some embodiments feeler portion 136 may comprise a channel. In some embodiments feeler portion 136 may comprise a notch.

In some embodiments the feeler portion 136 may include multiple indentations 138. In some embodiments the feeler portion 136 may include multiple channels. In some embodiments the feeler portion 136 may include multiple notches.

In some embodiments the indentation 138 may be less than a width of the arm portion 134. In some embodiments the indentation 138 may be less than every width of the arm portion 134. In some embodiments the indentation 138 may be greater than or equal to a width of the arm portion of 134. In some embodiments the indentation 138 may be greater than or equal to every width of the arm portion 134.

Figure 4D:
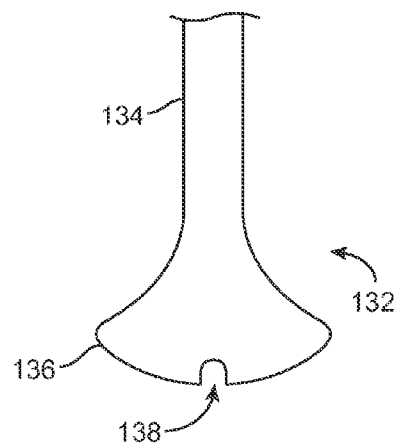

In some embodiments the profile of feeler portion 136 may be symmetric. In some embodiments the feeler portion 136 may be symmetric, including the indentation 138. In some embodiments the feeler portion may be symmetric about a line in the center of arm portion 134. In some embodiment the feeler portion 136 may be symmetric, as illustrated by FIG. 4D. In some embodiments, the arm portion 134 may be symmetric, as illustrated in FIG. 4B. In some embodiments the feeler portion 136 may have a symmetric profile. In some embodiments the feeler portion 136 may be asymmetric. In some embodiments the feeler portion 136 may be asymmetric, including the indentation 138. In some embodiments the indentation 138 may be asymmetric. In some embodiments the indentation 138 may be symmetric.

In some embodiments the projection 132 including a feeler portion 136 and indentation portion 138 may be configured such that the indentation 138 is configured to align the delivery system with a native commissure 612.

In some embodiments indentation 138 is configured such that the shape of indentation 138 is similar to a native commissural sinus 616. In some embodiments the indentation 138 is configured to have a shape different from a native commissural sinus 616. In some embodiments the indentation 138 may extend partially into the feeler portion 136. In some embodiments the indentation 138 may extend up to approximately half the length of the feeler portion 136. In some embodiments the indentation 138 may extend through the entire feeler portion 136. In some embodiments the indentation 138 can extend from the distal edge of the feeler portion 136 up into the arm portion 134. In some embodiments the indentation 138 stops before arm portion 134. In some embodiments the feeler portion may be configured to be shaped similar to a native commissural sinus 616.

In some embodiments the projection 132 is configured to provide tactile feedback regarding the location of a native commissure 612. In some embodiments the projection 132 is configured to provide tactile feedback regarding the location of a native commissural sinus 616. In some embodiments the projection 132 is configured to provide tactile feedback regarding the location of a native valve 614. In some embodiments the projection 132 is configured to provide tactile feedback regarding the location of a patient's heart 610.

In some embodiments, as illustrated in FIG. 4D, the projection 132 may be symmetric. In some embodiments the projection 132 may be asymmetric.

In some embodiments the feeler portion 136 is arc shaped. In some embodiments the feeler portion 136 has an indentation 138 along the distal edge. In some embodiments the feeler portion 136 is wider than the arm portion 134. In some embodiments the feeler portion 136 is narrower than the arm portion 134. In some embodiments the feeler portion 136 has indentations 138 along the distal edge.

In some embodiments the projection 132 is configured to be a hybrid or combination projection 132. In some embodiments the projection 132 is configured to have an arc shaped distal edge. In some embodiments the distal edge of a projection 132 is configured such that it is shaped to help align the delivery system within the native commissural sinus 616 of a patient's heart 610. In some embodiments the projection 132 has an indentation 138 to help provide tactile aid to the physician. In some embodiments the projection 132 is configured to allow for tactile feedback regarding the native commissural sinus 616 or native commissure 612. In some embodiments the projection 132 is configured to allow for tactile feedback regarding the native commissural sinus 616 and native commissure 612. In some embodiments the projection 132 is configured to allow for tactile feedback regarding the native valve 614. In some embodiments the projection 132 is configured to allow for tactile feedback regarding the patient's heart 610.

FIGS. 5A-5E illustrate some embodiments of the invention. In some embodiments the delivery system includes a catheter 100, an outer sheath 200, and handle 300. In some embodiments the delivery system may be configured to receive either or both of a medical device 400 and a prosthetic heart valve 500.

In some embodiments catheter 100 includes a tip 110, a capsule 120, and inner sheath 130. In some embodiments tip 100 is adjacent capsule 120. In some embodiments capsule 120 is adjacent inner sheath 130. In some embodiments tip 110 is substantially pointed and narrow. In some embodiments tip 110 has at least one portion of similar cross-sectional area along its length. In other embodiments tip 110 has a varying cross-sectional area along its length. In some embodiments tip 110 is adjacent capsule 120. In some embodiments the cross-sectional area of tip 110 increases from its distal most point to a point proximate capsule 120.

In some embodiments tip 110 and capsule 120 may be one integral part. In some embodiments tip 110 and capsule 120 may be two separate parts that are adjacent to one another. In some embodiments tip 110, capsule 120, inner sheath 130 may be one integral part. In some embodiments tip 110, capsule 120, and inner sheath 130 may all be separate parts. In some embodiments tip 110, capsule 120, and inner sheath 130 may be proximate one another.

In some embodiments tip 110 is proximate capsule 120. In some embodiments capsule 120 is proximate to inner sheath 130. In some embodiments capsule 120 is proximate to outer sheath 200. In some embodiments inner sheath 130 proximate or adjacent to handle 300. In some embodiments outer sheath 200 is proximate or adjacent handle 300.

In some embodiments outer sheath 200 is connected to handle 300. In some embodiments outer sheath 200 is coupled to handle 300. In some embodiments outer sheath 200 is joined to handle 300.

In some embodiments outer sheath 200 and handle 300 are an integral part. In some embodiments outer sheath 200 and handle 300 are separate parts.

In some embodiments handle 300 comprises an actuator 310. In some embodiments outer sheath 200 is adjacent to handle 300. In some embodiments actuator 310 is disposed on an end of handle 300. In some embodiments actuator 310 is disposed on a distal end of handle 300 proximate outer sheath 200. In some embodiments actuator 310 is disposed on a proximal end of handle 300 away from outer sheath 200. In some embodiments actuator 310 is disposed at a point along the length of the handle 300.

In some embodiments handle 300 includes varying cross-sectional areas. In some embodiments handle 300 a portion having a smaller cross-sectional area and a portion having a larger cross-sectional area. In some embodiments the portion having a larger cross-sectional area of handle 300 is disposed distal the end adjacent outer sheath 200. In some embodiments the portion having a larger cross-sectional area of handle 300 is disposed proximate the end adjacent outer sheath 200. In some embodiments handle 300 comprises a lumen through which a part or parts of the delivery system can pass through. In some embodiments handle 300 comprises a lumen through which a part or parts of the delivery system can move. In some embodiments the catheter 100 is threaded through the handle 300.

In some embodiments a portion of outer sheath 200 is surrounded by handle 300. In some embodiments a portion of outer sheath 200 is contained within handle 300. In some embodiments a portion of inner sheath 130 is surrounded by handle 300. In some embodiments a portion of inner sheath 130 is contained in handle 300.

In some embodiments handle 300 is a cylindrical shape. In some embodiments handle 300 has a cross-section similar to a square. In some embodiments handle 300 has a cross-section similar to a rectangle, triangle, oval, or other geometric shape.

In some embodiments handle 300 comprises one or more actuators 310. In some embodiments handle 300 comprises two or more actuators 310. In some embodiments handle 300 comprises actuators at different positions along a length of handle 300. In some embodiments actuators 310 are disposed at different points along the length of handle 300. In some embodiments one actuator is disposed on a proximal portion of handle 300. In some embodiments an actuator 310 is disposed on a distal portion of handle 300. In some embodiments one actuator 310 is disposed on a distal portion of handle 300, while another actuator is disposed on a proximal portion of handle 300. In some embodiments where three actuators 310 may be employed, each actuator may be disposed on a different portion of handle 300.

In some embodiments two actuators 310 are disposed on a portion of handle 300 with a first cross-sectional area. In some embodiments a third actuator 310 may be disposed on a portion of handle 300 with a second cross-sectional area.

In some embodiments actuators 310 may be actuated by a person. In some embodiments actuators 310 may be actuated using only one hand. In some embodiments actuators 310 may be actuated using one finger. In some embodiments when actuators are actuated outer sheath 200 is retracted, as illustrated in FIG. 5B. In some embodiments after actuator 310 is actuated outer sheath 200 is partially retracted. In some embodiments after actuator 310 is actuated outer sheath 200 is partially retracted and projection 132 or projections 132 may be exposed. In some embodiments actuators 310 may retract outer sheath 200.

In some embodiments actuator 310 may advance inner sheath 130. In some embodiments actuator 310 may advance projections 132. In some embodiments once projections 132 are advanced projections 132 begin to rotate radially outward. In some embodiments once projections 132 are advanced, projections 132 begin to flare outward. In some embodiments once projections 132 are advanced, projections 132 begin to move outward. In some embodiments when inner sheath 130 is advanced, projections 132 begin to open.

In some embodiments projections 132 may have a rectangular cross-sectional area. In some embodiments projections 132 may have a non-rectangular cross-sectional area. In some embodiments projections 132 may have a circular cross-sectional area. In some embodiments projections 132 may have an oval cross-sectional area. In some embodiments projections 132 may be curved on one side. In some embodiments projections 132 may be curved on two sides.

In some embodiments projections 132 can be advanced to at least partially cover capsule 120. In some embodiments projections 132 may be advanced to at least partially overlap with capsule 120. In some embodiments projections 132 are moved forward over at least a portion of capsule 120. In some embodiments after projections 132 are advanced capsule 120 is opened or retracted enough to anchor or position medical device 400. In some embodiments after projections 132 are advanced, capsule 120 is opened or retracted enough to anchor or position prosthetic heart valve 500. In some embodiments actuator 310 may retract support arms or projections 132 from the capsule area.

In some embodiments the delivery system including catheter 100 is configured to align a prosthetic heart valve 500 inside a patient's heart 610. In some embodiments one projection 132 may be coupled or attached to inner sheath 130. In some embodiments multiple projections 132 may be coupled or attached to inner sheath 130.

In some embodiments projection 132 includes an arm portion 134 or a feeler portion 136. In some embodiments projection 132 includes an arm portion 134 and a feeler portion 136. In some embodiments feeler portion 136 further comprises an indentation 138.

In some embodiments projections 132 are aligned with elements of medical device 400. In some embodiments projections 132 are aligned with elements of medical device 400 when projections 132 are proximate medical device 400. In some embodiments projections 132 are aligned with elements of medical device 400. In some embodiments projections 132 are aligned with elements of medical device 400 when projections 132 are disposed on or in capsule 120.

In some embodiments projections 132 are aligned with elements of prosthetic heart valve 500. In some embodiments portions of projection 132 are aligned with certain portions of prosthetic heart valve 500. In some embodiments projections 132 are aligned with two commissural posts 510 of prosthetic heart valve 500.

Figure 6:
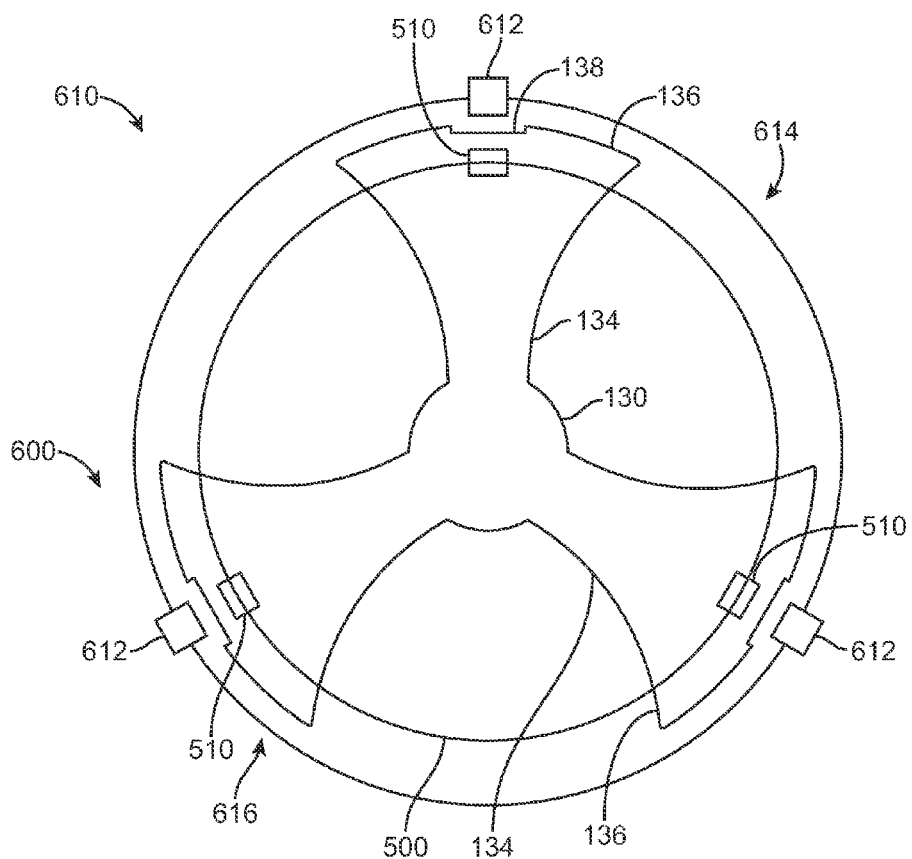
FIG. 6 illustrates a delivery system relative to a patient's heart in accordance with some embodiments.

A patient heart 610 may comprise native commissures 612, native valves 614, and native commissural sinuses 616. As can be seen in FIG. 6, when projections 132 are extended toward a patient's heart 610 the projections 132 are configured to aid in positioning the prosthetic heart valve 500 inside the patient's heart 610.

In some embodiments, as illustrated in FIG. 6, the projections 132 may be aligned with one or more commissural posts 510. In some embodiments the projections 132 may be aligned with one or more native commissures 612. In some embodiments, as illustrated by FIG. 6A, projections 132 may include feeler portions 136 configured such that feeler portions 136 are similar in shape to a portion of patient's heart 610. Projections 132 may include feeler portions 136 configured such that feeler portions 136 are substantially similar in shape to a portion of the native valves 614 or a portion of a native commissural sinus 616. In some embodiments a projection 132 comprises a feeler portion 136 and an indentation 138. In some embodiments indentation 138 is configured to receive a native commissure 612. In some embodiments the shape of indentation 138 provides for specific alignment of prosthetic heart valve 500 within patient heart 610. As illustrated in FIG. 6, the delivery system may include multiple projections 132 configured to align the prosthetic heart valve 500 with patient heart 610. In some embodiments, the delivery system may only comprise one projection 132 for aligning prosthetic heart valve 500 with patient's heart 610. In some embodiments there may be exactly two projections 132 for aligning prosthetic heart valve 500 with patient's heart 610.

In some embodiments a patient may require a valve-in-valve medical procedure wherein a second prosthetic heart valve is positioned and implanted within a previously implanted prosthetic heart valve. In some embodiments the previously implanted prosthetic heart valve may be, for example, a surgical valve, a tissue valve, a mechanical valve, a suture-less surgical valve, a stented valve, a non-stented valve, a transcatheter valve, a balloon expandable valve, a mechanically expandable valve a, and/or a self-expandable valve. In some embodiments patient heart 610 may comprise one or more prosthetic heart valves previously implanted during one or more previous medical procedures. In some embodiments projections 132 may be configured to aid in positioning medical device 400 and/or prosthetic heart valve 500 inside patient heart 610 comprising a prosthetic valve implanted in a previous medical procedure. In some embodiments projections 132 may be aligned with one or more portions of a previously implanted prosthetic heart valve such as one or more commissural posts of a previously implanted prosthetic heart valve.

Projections 132 may include feeler portions 136 configured such that feeler portions 136 are substantially similar in shape to one or more portions of a previously implanted prosthetic heart valve. In some embodiments a projection 132 comprises a feeler portion 136 and an indentation 138. In some embodiments indentation 138 is configured to receive a prosthetic heart valve commissure. In some embodiments the shape of indentation 138 provides for specific alignment of medical device 400 and/or prosthetic heart valve 500 within a prosthetic heart valve within patient heart 610.

In some embodiments the delivery system may include multiple projections 132 configured to align medical device 400 and/or prosthetic heart valve 500 with a prosthetic heart valve previously implanted in patient heart 610. In some embodiments the delivery system may only comprise one projection 132 for aligning medical device 400 and/or prosthetic heart valve 500 with a prosthetic heart valve previously implanted in patient heart 610. In some embodiments there may be exactly two or three projections 132 for aligning medical device 400 and/or prosthetic heart valve 500 with a prosthetic heart valve previously implanted in patient heart 610. In some embodiments there may be more than three projections 132 for aligning medical device 400 and/or prosthetic heart valve 500 with a prosthetic heart valve previously implanted in patient heart 610.

In some embodiments a patient may require a medical procedure wherein a prosthetic heart valve is positioned and implanted within a previously implanted medical device such as a prosthetic heart valve repair device including, for example an annuloplasty ring or annuloplasty band device. In some embodiments a patient may require a valve-in-ring medical procedure. In some embodiments the previously implanted prosthetic heart valve repair device may be, for example, an annuloplasty device, an annuloplasty ring device, an annuloplasty band device, a prosthetic heart valve support device, and/or a prosthetic heart valve anchor device. In some embodiments patient heart 610 may comprise one or more prosthetic heart valve repair devices previously implanted during one or more previous medical procedures.

In some embodiments projections 132 may be configured to aid in positioning medical device 400 and/or prosthetic heart valve 500 inside patient heart 610 comprising a prosthetic valve repair device implanted in a previous medical procedure. In some embodiments projections 132 may be aligned with one or more portions of a previously implanted prosthetic heart valve repair device. Projections 132 may include feeler portions 136 configured such that feeler portions 136 are substantially similar in shape to one or more portions of a previously implanted prosthetic heart valve repair device.

In some embodiments the shape of projection 132 may provide for specific alignment of medical device 400 and/or prosthetic heart valve 500 within a prosthetic heart valve repair device within patient heart 610. In some embodiments the delivery system may include multiple projections 132 configured to align medical device 400 and/or prosthetic heart valve 500 with a prosthetic heart valve repair device previously implanted in patient heart 610. In some embodiments the delivery system may only comprise one projection 132 for aligning medical device 400 and/or prosthetic heart valve 500 with a prosthetic heart valve repair device previously implanted in patient heart 610. In some embodiments there may be exactly two or three projections 132 for aligning medical device 400 and/or prosthetic heart valve 500 with a prosthetic heart valve repair device previously implanted in patient heart 610.

In some embodiments projections 132 may have shapes different from one another. In embodiments with multiple projections 132, one projection 132 may have a curved distal edge similar to a native commissural sinus 616 in a patient's heart 610. Another projection 132 may have a distal edge that is substantially straight. Another projection 132 may have a distal edge that includes indentation 138.

In some embodiments the profile of projections 132 may vary even when projections 132 may be part of the same delivery system. In some embodiments the shape of projections 132 may vary even when projections 132 may be part of the same delivery system. In some embodiments, a first projection 132 may have a shape different from a second projection 132. In some embodiments, a first projection 132 may have a shape different from a second projection 132 and different from a third projection. In some embodiments, a second projection 132 may have a shape different from a third projection 132. In some embodiments, all projections 132 have a shape different from every other projection 132. In some embodiments one projection 132 comprises a feeler portion 136 that is wider than a feeler portion 136 on a second projection 132. In some embodiments a first projection 132 may have an arm portion 134 that is wider than an arm portion 134 on a second projection 132.

The foregoing description has been presented for purposes of illustration and description. It is not intended to be exhaustive or to limit the precise embodiments disclosed. Other modifications and variations may be possible in light of the above teachings. The embodiments and examples were chosen and described in order to best explain the principles of the embodiments and their practical application, and to thereby enable others skilled in the art to best utilize the various embodiments with modifications as are suited to the particular use contemplated. By applying knowledge within the skill of the art, others can readily modify and/or adapt for various applications such specific embodiments, without undue experimentation, without departing from the general concept. Therefore, such adaptations and modifications are intended to be within the meaning and range of equivalents of the disclosed embodiments, based on the teaching and guidance presented herein.

What is claimed is:

1. A system for delivering a medical device, the system comprising:
    a catheter, the catheter comprising:
    a tip;
    a capsule having a distal end adjacent the tip and being configured to receive a medical device in a collapsed configuration, wherein the capsule is configured to be proximally retracted relative to the tip to release the medical device;
    an inner sheath having a distal end that comprises a plurality of projections disposed adjacent the capsule, the inner sheath being disposed to extend along a longitudinal axis of the catheter and the projections being configured to open outwardly relative to an outer surface of the capsule, wherein each projection comprises an arm portion and a feeler portion, the feeler portion having a proximal end adjacent the arm portion and a distal end spaced from the arm portion, wherein at least a portion of the feeler portion is wider than the arm portion; and
    an outer sheath disposed along the longitudinal axis of the catheter to slidably extend over the inner sheath, the outer sheath being connected to a handle, the handle further comprising an actuator,
    wherein the actuator is configured to actuate the outer sheath relative to the inner sheath to expose the projections and to thereby permit the projections to open outward such that the projections are radially spaced about at least a proximal end of the capsule.

2. The system of claim 1, wherein the projections are asymmetric.

3. The system of claim 1, wherein the projections are configured to be evenly spaced from each other when they open outward.

4. The system of claim 1, wherein the feeler portion has a substantially straight distal end.

5. The system of claim 1, wherein the feeler portion comprises protrusions extending away from the arm portion.

6. The system of claim 1, wherein the distal end of the feeler portion comprises a curved end, and wherein the curved end further comprises a notch.

7. The system of claim 1, wherein the feeler portion is symmetric.

8. The system of claim 1, wherein the feeler portion is asymmetric.

9. The system of claim 1, wherein distal ends of the plurality of projections are unattached to a remainder of the catheter.

10. The assembly of claim 1, wherein the outer sheath is actuated to be proximally retracted relative to the inner sheath to expose the projections and to permit the projections to open outward such that the projections are radially spaced about at least the proximal end of the capsule.

11. The assembly of claim 10, wherein when the outer sheath is proximally retracted such that the projections open outward, the capsule is configured to remain in the same position such that the medical device remains in the collapsed configuration therein.

12. A system for delivering a medical device, the system comprising:
    a catheter, the catheter comprising:
    a tip;
    a capsule adjacent the tip;
    an inner sheath adjacent the capsule, the inner sheath being disposed along a longitudinal axis; and
    an outer sheath disposed along the longitudinal axis and connected to a handle, the handle further comprising an actuator,
    wherein the inner sheath comprises projections distal the handle,
    wherein the actuator is configured to actuate the outer sheath,
    wherein the capsule is configured to receive a medical device,
    wherein the outer sheath is configured to move along the longitudinal axis to expose the projections,
    wherein the projections are configured to open outward from the longitudinal axis, and
    wherein each projection is uniquely shaped.

13. An assembly for delivering a prosthetic heart valve, the assembly comprising:
    a tip;
    a capsule configured to receive a prosthetic heart valve in a collapsed configuration therein and configured to be proximally retracted relative to the tip to release the prosthetic heart valve;
    an inner sheath comprising a plurality of projections that are configured to extend away from an outer surface of the capsule, the inner sheath being disposed along a longitudinal axis of the assembly, wherein at least one of the plurality of projections further comprises an indentation on a distal most edge, and wherein the projection comprises a shape made from wire; and
    an outer sheath being disposed along the longitudinal axis of the assembly over the inner sheath and being coupled to a handle, wherein the handle further includes an actuator that is configured to actuate the outer sheath relative to the inner sheath to expose the projections and to permit the projections to extend away from the outer surface of the capsule.

14. The assembly of claim 13, wherein at least one of the projections is configured to be positioned relative to a native commissure by using fluoroscopic imaging.

15. The assembly of claim 13, wherein at least one of the projections further comprises an asymmetric shape.

16. The assembly of claim 13, wherein distal ends of the plurality of projections are unattached to a remainder of the assembly.

17. The assembly of claim 13, wherein the outer sheath is actuated to be proximally retracted relative to the inner sheath to expose the projections and to permit the projections to extend away from the outer surface of the capsule.

18. The assembly of claim 17, wherein when the outer sheath is proximally retracted such that the projections extend away from the outer surface of the capsule, the capsule is configured to remain in the same position such that the prosthetic heart valve remains in the collapsed configuration therein.

* * * * *